United States Patent [19]

Motoike et al.

[11] Patent Number: 4,850,024

[45] Date of Patent: Jul. 18, 1989

[54] METHOD AND APPARATUS FOR CLASSIFYING WHITE BLOOD CELLS

[75] Inventors: Jun Motoike; Akihide Hashizume, both of Hachioji; Ryuichi Suzuki, Koganei, all of Japan

[73] Assignee: Hitachi, Ltd., Tokyo, Japan

[21] Appl. No.: 720,013

[22] Filed: Apr. 4, 1985

[30] Foreign Application Priority Data

Apr. 5, 1984 [JP] Japan ................... 59-68082

[51] Int. Cl.⁴ .............................................. G06K 9/00
[52] U.S. Cl. .................................. 382/6; 364/413.08; 356/39
[58] Field of Search ...................... 382/6, 36; 364/416; 356/39; 377/6, 10

[56] References Cited

U.S. PATENT DOCUMENTS

| | | | |
|---|---|---|---|
| 3,827,804 | 8/1974 | Miller et al. | 382/6 |
| 3,832,687 | 8/1974 | Miller et al. | 382/6 |
| 3,999,047 | 12/1976 | Green | 382/6 |
| 4,045,655 | 8/1977 | Suzuki et al. | 364/416 |
| 4,183,013 | 1/1980 | Agrawala et al. | 377/10 |
| 4,307,376 | 12/1981 | Miller et al. | 382/6 |

OTHER PUBLICATIONS

Bacus et al., "Leukocyte Pattern Recognition", *IEEE Transactions on Systems, Man, and Cybernetics*, vol. SMC-2, No. 2, Sep. 1972.

*Primary Examiner*—Leo H. Boudreau
*Assistant Examiner*—Joseph Mancuso
*Attorney, Agent, or Firm*—Antonelli, Terry & Wands

[57] ABSTRACT

An apparatus for classifying leukocytes comprises a sample image preprocessing unit which modifies the pattern of the nucleus of each of predetermined number of leukocytes extracted from the image of a blood sample, a unit for analyzing each of the processed nucleus patterns and broadly classifying each of the leukocytes into a typical or quasi-typical band form neutrophil, a typical or quasi-typical segmented neutrophil, or other neutrophil in an intermixture domain or a leukocyte other than a neutrophil, and a unit for calculating sample estimation indexes from the numbers of typical and quasi-typical neutrophils and the total number of neutrophils, classifying each of the neutrophils in the intermixture domain into a band form or a segmented neutrophil in accordance with the estimation indexes, and adding the numbers of intermixed band form and segmented neutrophils to the numbers of typical or quasi-typical band form and segmented neutrophils, respectively.

9 Claims, 8 Drawing Sheets

100
METHOD AND APPARATUS FOR CLASSIFYING WHITE BLOOD CELLS

BACKGROUND OF THE INVENTION

The present invention relates to a method and apparatus for classifying white blood cells (leukocytes) and, particularly, to a leukocyte classifying apparatus capable of automatically classifying neutrophils into band form neutrophils and segmented neutrophils accurately.

Blood cells are produced in the marrow, and they have various forms in each phase of growth and ultimately flow in peripheral blood. Blood cells include leukocytes, erythrocytes and thrombocytes. Leukocytes have structural information which indicates the presence or absence of blood diseases such as leukemia and other diseases.

Figure 1:
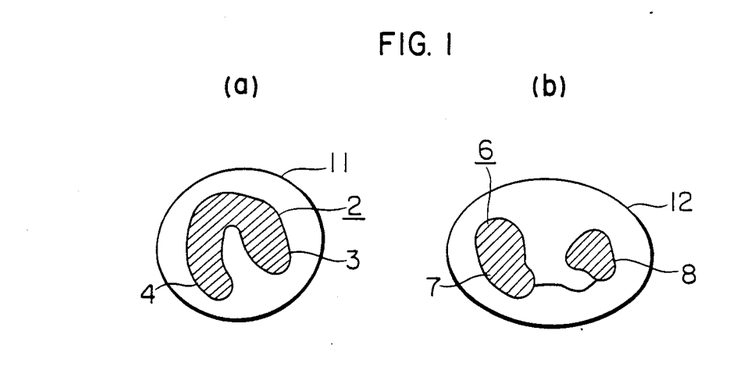
FIG. 1 is a set of illustrations showing a band form neutrophil and a segmented neutrophil.

Classification of leukocytes is to classify grown leukocytes or detect and classify immature leukocytes using smeared and stained blood samples. Grown leukocytes fall into neutrophils, eosinophils, basophils, monocytes and lymphocytes. Neutrophils, which amount to about 55% of human peripheral blood, are subdivided into band form neutrophils 11 each having a single nucleus as shown in (a) of FIG. 1 and segmented neutrophils 12 with its nucleus constricted and separated into two or more as shown in (b) of FIG. 1. The ratio of the quantities of the two types of neutrophils is related to the blood diseases, and therefore it is necessary to classify neutrophils accurately.

Figure 2:
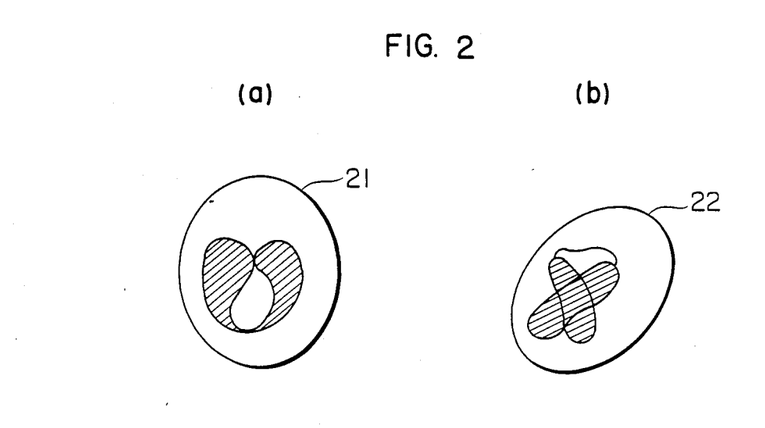
FIG. 2 is a set of illustrations showing segmented neutrophils having a linking nucleus and an overlapping nucleus, respectively.

One method of classifying neutrophils is based on the count of nucleus mask pattern components, $N_c$, calculated by the nucleus mask pattern extraction method to determine each nucleus to be a band form nucleus when $N_c=1$, or to be a segmented nucleus when $N_c \geq 2$. Namely, when a nucleus mask pattern 2 consists of two islands 3 and 4 linked by a broad bridge, as shown in (a) of FIG. 1, the islands 3 and 4 are assumed to constitute in combination one component, and when a nucleus mask pattern 6 consists of two islands 7 and 8 linked by a narrow bridge as shown in (b) of FIG. 2, each of the islands 3 and 4 is assumed to constitute one component. The method of extracting a nucleus mask pattern is disclosed in Japanese Patent Application Laid-open No. 53-13491, and the method of counting components of a nucleus mask pattern is disclosed in Japanese Patent Application Laid-open No. 51-95799.

There has been proposed a modified method in which the above-mentioned classifying method is added by the process for detecting holes in the nucleus mask pattern caused by the improper contrast of the nucleus image and for filling the holes, and the process for separating bridged components of a segmented neutrophil. This method has been realized on an approximation basis through the process of coarse sampling of a nucleus mask pattern, as disclosed in Japanese Patent Application Laid-open No. 53-52495. All of the foregoing methods, however, are apt to determine the number of pattern components to be $N_c=1$ for the cases of a segmented neutrophil 21 with its islands of nucleus in contact with each other as shown in (a) of FIG. 2, or a segmented neutrophil 22 with its islands of nucleus overlapping as shown in (b) of FIG. 2. On this account, if links or overlaps of islands occur in increased proportion in neutrophils by some reason, the accuracy of classification is impaired. The coincidence between the manual classification of neutrophils and the above-mentioned conventional automatic classification is 74%, and the accuracy of automatic classification technique is not yet satisfactory.

SUMMARY OF THE INVENTION

It is an object of the present invention to overcome the foregoing prior art deficiencies and to provide a leukocytes classifying method and apparatus capable of classifying neutrophils into band form neutrophils and segmented neutrophils accurately irrespective of the frequency of occurrence of links and overlaps of nucleus islands.

In order to achieve the above objective, the inventive leukocytes classifying apparatus comprises a sample image preprocessing unit for modifying the pattern of the nucleus of each of predetermined number of leukocytes extracted from the image of a blood sample, a unit for analyzing each of the processed nucleus patterns and broadly classifying each of the leukocytes into a typical or quasi-typical band form neutrophil, a typical or quasi-typical segmented neutrophil, or other neutrophil in an intermixture domain or a leucocyte other than a neutrophil, and a unit for calculating sample estimation indexes from the numbers of typical and quasi-typical neutrophils and the total number of neutrophils, classifying each of the neutrophils in the intermixture domain into a band form or a segmented neutrophil in accordance with the estimation indexes.

DESCRIPTION OF THE PREFERRED EMBODIMENT

The principle and an embodiment of the present invention will now be described with reference to the drawings. FIGS. 3 through 11 are used to explain the principle of this invention.

The principle of this invention is as follows. First, typical and quasi-typical band form neutrophils and typical and quasi-typical segmented neutrophils are defined, all of neutrophils are classified into groups of typical and quasi-typical neutrophils and another group of other neutrophils in the intermixture domain, and the numbers of the typical neutrophils and quasi-typical neutrophils are counted. Next, an estimation index for the neutrophils in the intermixture domain is set up basing on the above counts, and the neutrophils in the intermixture domain are classified into band form neutrophils and segmented neutrophils. This procedure enables accurate discrimination between band form and segmented neutrophils for those in which nucleus islands link or overlap with each other.

Figure 3:
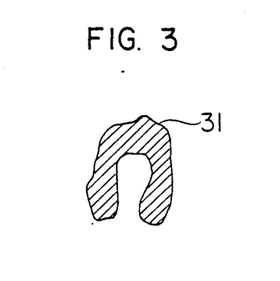
FIG. 3 is an illustration showing a nucleus of a typical band form neutrophil.
Figure 4:
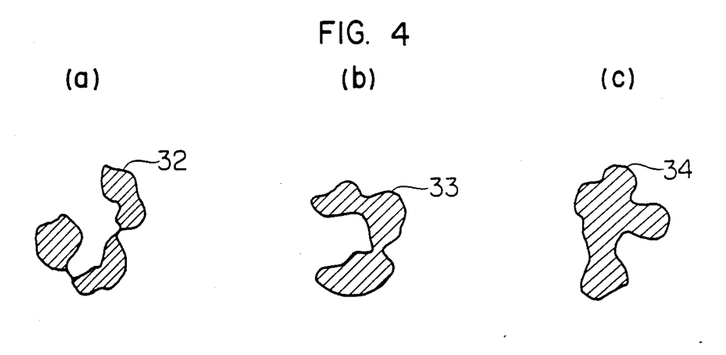
FIG. 4 is a set of illustrations showing nuclei of typical segmented neutrophils.

FIG. 3 shows an example of the nucleus of a typical band form neutrophil, and FIG. 4 shows examples of the nucleus of a typical segmented neutrophil. A typical band form neutrophil is defined here to be one that has a single inlet with its area ratio, i.e., the ratio of the area of the inlet to the total area of the nucleus as will be described shortly, larger than a certain value. A typical segmented neutrophil is defined here to be one that has completely separate nucleus or such a nucleus 32 whose islands are connected to each other through a very narrow bridge as shown in (a) of FIG. 4, one that has a constricted section of the nucleus 33 thinner than a certain value as shown in (b) of FIG. 4, or one that has a nucleus 34 with the shape of λ, x or T as shown in (c) of FIG. 4. These typical neutrophils can be identified by analyzing each neutrophil using the nucleus mask pattern extraction method.

Figure 5:
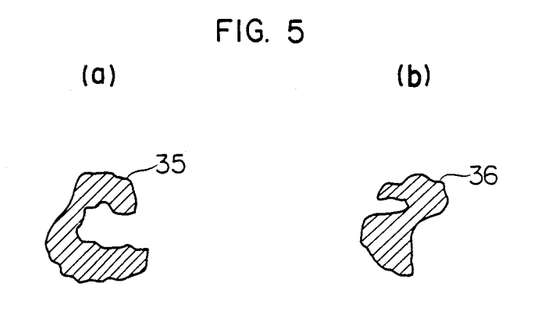
FIG. 5 is a set of illustrations showing nuclei of quasi-typical neutrophils.

The following describes the method of identifying quasi-typical band form and segmented neutrophils in a sample (neutrophils) in which typical neutrophils have already been identified. (a) of FIG. 5 shows an example of the nucleus of a quasi-typical band form neutrophil, and (b) of FIG. 5 shows an example of the nucleus of a quasi-typical segmented neutrophil.

First, the 'circularity' of a circumscribed polygon for the nucleus as defined by the following expression (1) and the inlet-to-total area ratio as defined by the following expression (2) are calculated for each neutrophil.

$$\text{Circularity} = \frac{K(\text{Area of circumscribed polygon})}{(\text{Periphery of circumscribed polygon})^2} \quad (1)$$

where K is a modification factor.

$$\text{Area ratio} = \frac{\text{Total area of inlets}}{\text{Area of circumscribed polygon}} \quad (2)$$

The area and periphery of the circumscribed polygon and the total area of inlets are evaluated as follows.

Figure 6:
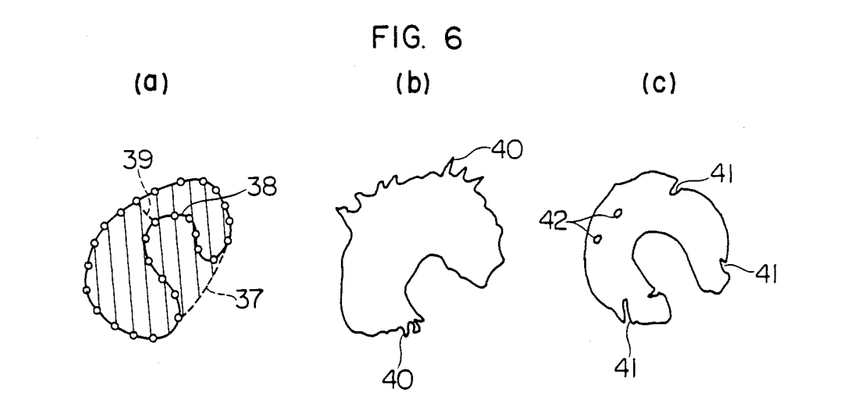
FIG. 6 is a set of illustrations used to explain the method of measuring the ratio of areas and ratio of lengths of an inlet and the method of the hole filling process and the thinning process.

A neutrophil is viewed microscopically with an optoelectric transducing device such as a television camera, and the analog image signal is converted into the digital signal to produce image data. Basing on the image data, a polygon in contact externally to the image of a nucleus of the neutrophil is formed. (a) of FIG. 6 shows an example of such a polygon, which as shown by hatching includes an inlet. An inner polygon, which is defined by sides 38 and a side 37 common to the circumscribed polygon, is determined to be an inlet when the ratio of the length of the sides 38 to the length of the common side 37 is large. The area of the circumscribed polygon is the area of the hatched portion in (a) of FIG. 6, and the periphery of the polygon is the length of the periphery of the hatched portion.

Neutrophils with the area ratio larger than 0.11 as calculated using the expression (2) are counted in a group of quasi-typical band form or segmented neutrophils. When a neutrophil has a plurality (more than two) of inlets, they are named the first inlet, the second inlet, the third inlet, and so on in the order of side.

Neutrophils counted in the group of quasi-typical band form or segmented neutrophils are classified by the following three methods.

(1) Classification based on information on the first and second inlets

If the following expression (3) or (4) is satisfied, the neutrophil is determined to be a quasi-typical neutrophil.

$$A_1/TA < T_0 \quad (3)$$

$$D_2/C_2 < T_1 \quad (4)$$

where
$A_1$: area of the first inlet;
TA: total area of inlet;
$D_2$: length of common side of inner polygon of the second inlet;
$C_2$: length of all sides excluding the common side of inner polygon of the second inlet;
$D_2/C_2$ ratio of lengths of the second inlet;
$T_0, T_1$ reference values determined from the circularity calculated by expression (1).

Figure 7:
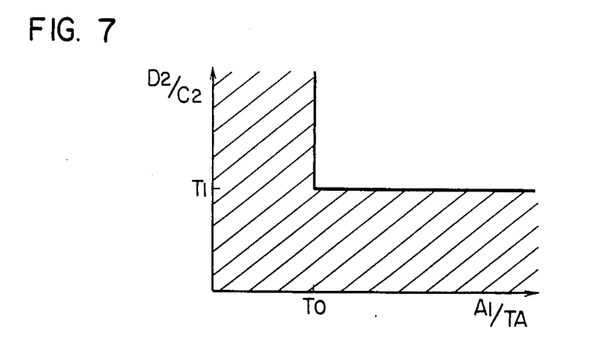
FIGS. 7, 8 and 9 are diagrams each showing classified regions for quasi-typical band form neutrophils and segmented neutrophils.

The region satisfying the conditions of expressions (3) and (4) is indicated by hatching in FIG. 7.

(2) Classification based on information on the second and third inlets

If the following expressions (5) and (6) are satisfied, the neutrophil is determined to be a quasi-typical segmented neutrophil.

$$a \cdot A_2/D_2 + b \cdot A_3/D_3 + c \geq 0 \quad (5)$$

$$A_3/D_3 \geq d \quad (6)$$

where
$A_2, A_3$ areas of the second and third inlets;
$D_2, D_3$ lengths of common sides of inner polygons of the second and third inlets;
a,b,c,d : reference values.

Figure 8:
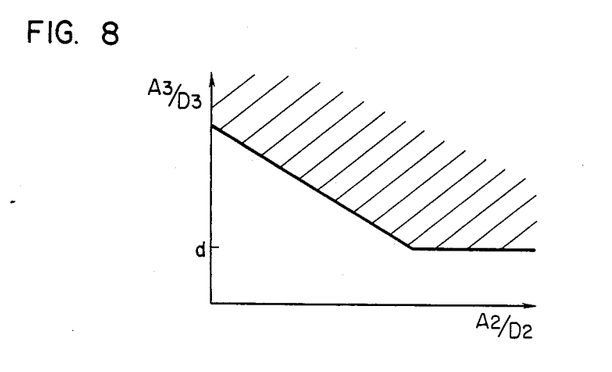

The region satisfying the conditional expressions (5) and (6) is indicated by hatching in FIG. 8.

(3) Classification based on information on the first inlet

If the following expressions (7), (8) and (9) are satisfied, the neutrophil is determined to be a quasi-typical band form neutrophil.

$$p \cdot A_1/TD + q \cdot A_1/TA + r > 0 \quad (7)$$

$$s \leq A_1/TD \leq t \quad (8)$$

$$u \leq R < v \quad (9)$$

where
TD: area of circumscribed polygon;
R: minimum width of the nucleus (see 39 in (a) of FIG. 6);
p,q,r,s,t,u,v: reference values (p, q and r are determined from the circularity).

Figure 9:
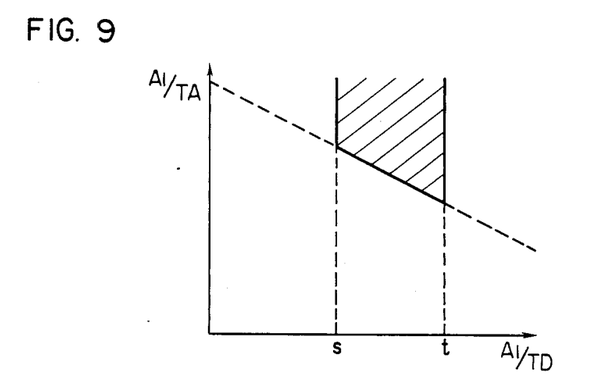

The region satisfying the conditional expressions (7), (8) and (9) is indicated by hatching in FIG. 9.

The above expressions (3) through (9) and the reference values are derived from the experimental manual classification of neutrophils.

Figure 10:
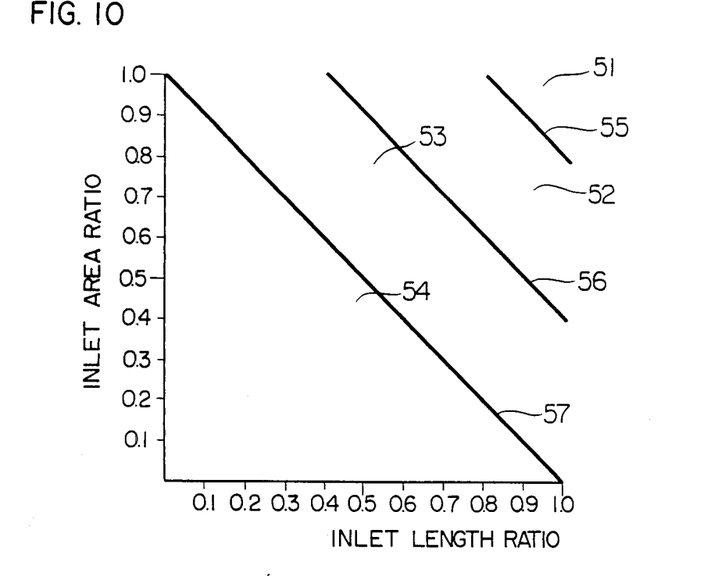
FIG. 10 is a diagram showing the neutrophils classification logic in the intermixture domain.
Figure 11:
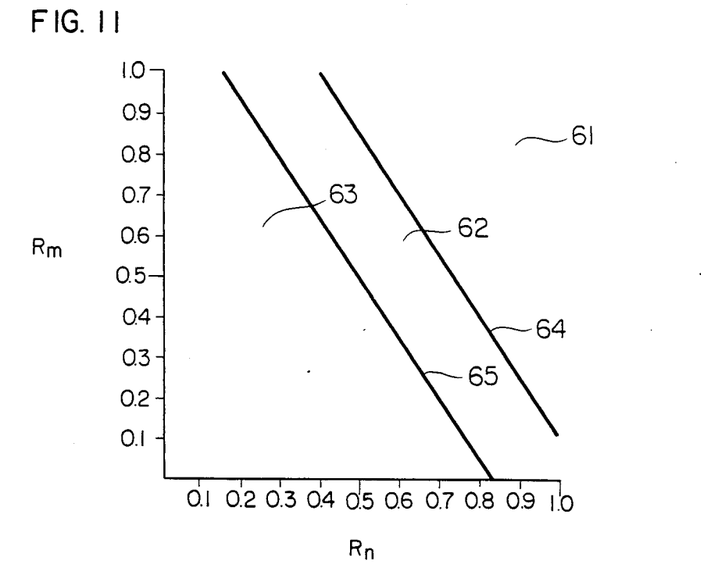
FIG. 11 is a diagram showing the logic of evaluating the estimation index for the sample.

The following describes the method of classifying the remaining unknown neutrophils in the intermixture domain, i.e., neutrophils out of the foregoing classified groups of typical and quasi-typical band form and segmented neutrophils, into band form neutrophils and segmented neutrophils. FIG. 10 shows the logic for classifying neutrophils in the intermixture domain, and FIG. 11 shows the logic for obtaining the estimation indices for samples.

First, the length ratio and area ratio for the inlet of a neutrophil in the intermixture domain are calculated and plotted, the length ratio on the abscissae and the area ratio on the ordinate, on the graph of FIG. 10.

Next, as to whether the plotted neutrophil is a band form neutrophil or a segmented neutrophil is determined basing on selected one of thresholds 55, 56 and 57. For example, when the threshold 55 is used, a neutrophil located in a region 51 is determined to be a band form neutrophil, while one located in a region 52, 53 or 54 is determined to be a segmented neutrophil. Similarly, when the threshold 56 is used, a neutrophil located in the region 51 or 52 is determined to be a band form neutrophil, while one located in the region 53 or 54 is determined to be a segmented neutrophil. And, when the threshold 57 is used, a neutrophil located in the region 51, 52 or 53 is determined to be a band form neutrophil, while one located in the region 54 is determined to be a segmented neutrophil. Which one of the thresholds 55, 56 and 57 is to be selected for use is determined from the presumption space shown in FIG. 11. FIG. 11 is a graph with its abscissae representing the ratio Rn of the number of typical and quasi-typical segmented neutrophils to the total number of neutrophils, and with its ordinate representing the ratio Rm of the number of typical and quasi-typical segmented neutrophils to the sum of the numbers of typical and quasi-typical band form and segmented neutrophils. The ratios Rn and Rm are expressed by the following equations.

$$Rn = \frac{St + Sq}{N} \quad (10)$$

$$Rm = \frac{St + Sq}{St + Sq + Bt + Bq} \quad (11)$$

where St represents the number of typical segmented neutrophils, Sq is the number of quasi-typical segmented neutrophils, N is the total number of neutrophils, Bt is the number of typical band form neutrophils, and Bq is the number of quasi-typical band form neutrophils.

The sample presumption space is divided into, for example, three sub-spaces including a region 61 for samples with a smaller number of band form neutrophils, a region 62 for samples with a fairly large number of band form neutrophils and a region 63 with an extremely large number of band form neutrophils. The three regions of the sample presumption space are separated from each other by thresholds 64 and 65.

Depending on which of the regions 61, 62 and 63 in the presumption space of FIG. 11 the values Rn and Rm of equations (10) and (11) belong to, one of the thresholds 55, 56 and 57 in FIG. 10 is selected. In case the values Rn and Rm belong to the region 61 of the presumption space, i.e., for samples with a smaller proportion of band form neutrophils, the threshold 55 in FIG. 10 is used, and only neutrophils located in the region 51 are determined to be band form neutrophils, while ones located in the regions 52, 53 and 54 are determined to be segmented neutrophils. In case the values Rn and Rm belong to the region 62 in the presumption space of FIG. 11, i.e., for samples with a relatively large proportion of band form neutrophils, the threshold 56 is used, and neutrophils located in the regions 51 and 52 are determined to be band form neutrophils, while ones located in the regions 53 and 54 are determined to be segmented neutrophils. In case the values Rn and Rm belong to the region 63 in the presumption space of FIG. 11, i.e., for samples with a larger proportion of band form neutrophils, the threshold 57 is used, and neutrophils located in the regions 51 and 52 of FIG. 10 are determined to be band form neutrophils, while ones located in the regions 53 and 54 are determined to be segmented neutrophils. Thus, the optimal selection of the classification regions reflecting the type of samples is made possible.

The thresholds 55, 56, 57, 64 and 65 shown in FIGS. 10 and 11 are derived from the experimental manual classification of neutrophils, and this scheme allows classification of neutrophils in the intermixture domain with an accuracy of about 83%.

Although in FIG. 11 the sample presumption space is divided into three regions, this invention is not limited to this, but the space may be divided into four or more regions so that the graph of FIG. 10 has five or more identification regions, or the space may be estimated continuously so that the graph of FIG. 10 provides continuous resultant values. Thus neutrophils are classified into two groups by the multi-threshold classification logic that is based on the numbers of typical and quasi-typical band form and segmented neutrophils.

Figure 12:
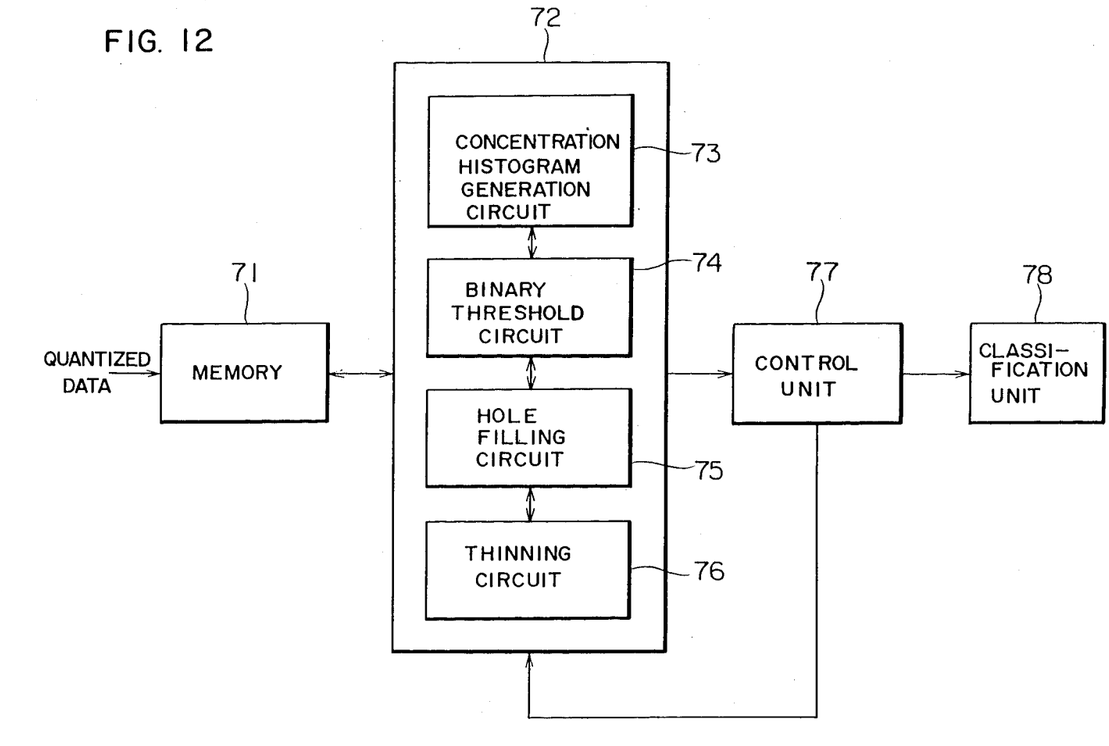
FIG. 12 is a block diagram showing the leukocytes classifying apparatus embodying the present invention.
Figure 14:
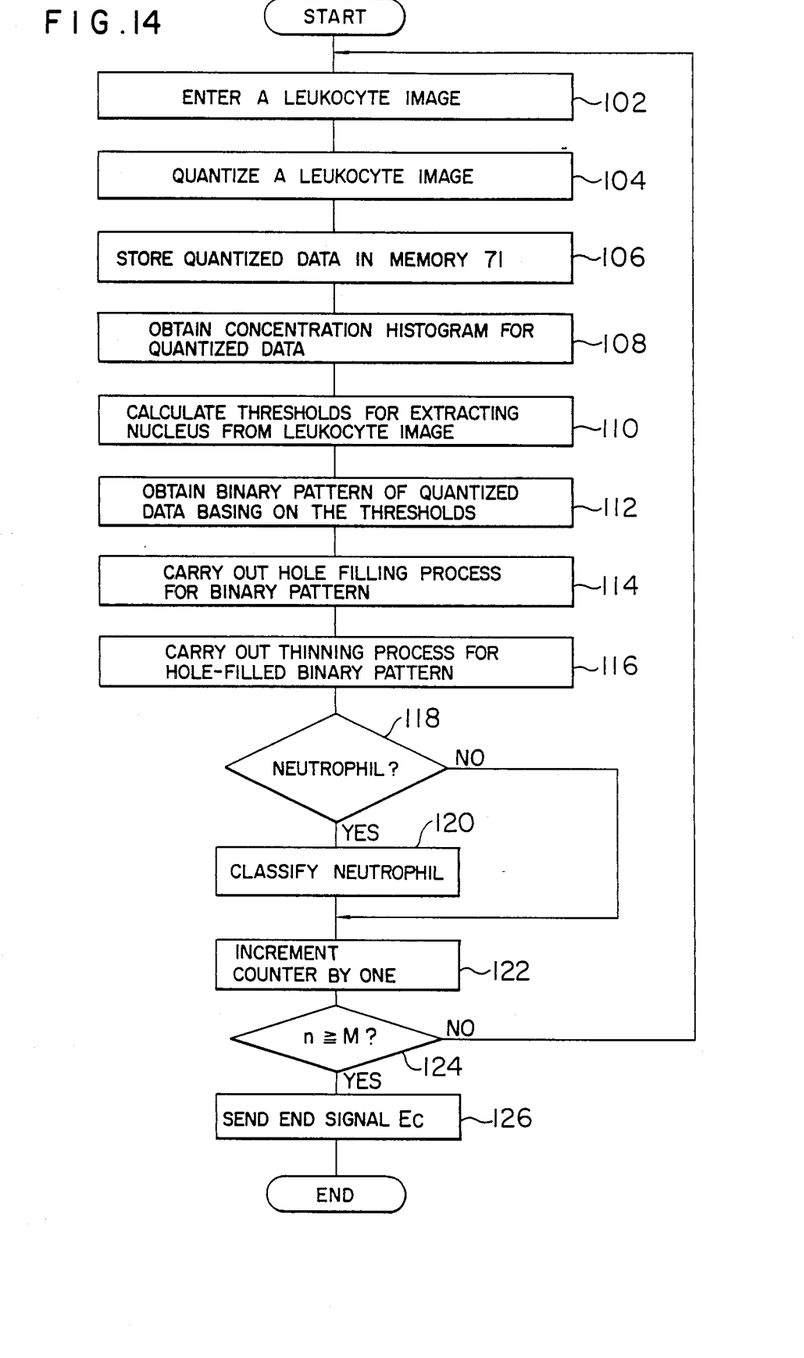
FIGS. 14 and 15 are flowcharts used to explain the operation of the control unit 77 shown in FIG. 12.

FIG. 12 shows in block diagram an embodiment of the inventive leukocytes classification apparatus. The apparatus consists of a memory 71, an image preprocessing unit 72, a control unit 77 and a classification unit 78. The arrangement and operation of the apparatus, which is intended to classify leukocytes of a certain number M in this embodiment, will be described by making reference to FIGS. 14 and 15 that explain the operation of the control unit 77.

A leukocyte is viewed microscopically with an optoelectric transducing device (not shown), and, after the analog image signal is quantized with an analog-to-digital converter (not shown) (steps 102 and 104), the quantized image of the leukocyte is stored in the memory 71 (step 106). The memory 71 is made up of a plurality of 1-frame memory cells. The image preprocessing unit 72 consists of a concentration histogram generation circuit 73, a binary threshold circuit 74, a hole filling circuit 75 and a thinning circuit 76. All of these component circuits are known, and they are disclosed in, for example, publication entitled "Digital Picture Processing", A. Rosenfeld and A.C. Kak, 1976, Academic Press.

Initially, the signal from the memory 71 is entered to the concentration histogram generation circuit 73 in the preprocessing unit 72 so that a concentration histogram is produced (step 108). The histogram is delivered to the control unit 77, which calculates the threshold value suitable for extracting the nucleus of the leukocyte (step 110). The control unit 77 is arranged by inclusion of a microcomputer. The nucleus extracting threshold value calculated by the control unit 77 is delivered to the binary threshold circuit 74 in the preprocessing unit 72. The binary threshold circuit 74 receives and latches the threshold value as a reference value.

Next, data stored in the memory 71 is read out into the binary threshold circuit 74 so that a binary pattern of the nucleus is produced from the data in accordance with the threshold value (step 112), and the result is stored in the memory 71.

Subsequently, the binary pattern in the memory 71 is read out into the hole filling circuit 75 in the preprocessing unit 72. The hole filling circuit 75 operates to fill small holes in the binary pattern, such as holes 41 and 42 shown in (c) of FIG. 6, so as to facilitate the following process. The hole filling process is a process performed for a partial area of, for example, a 3-by-3 pixel matrix of the binary pattern, in which if eight points out of nine (all points of the pixel matrix excluding the central point in question) have values of "1" in a reasonable relationship between one another, the point in question is made to have a "1" value irrespective of its original value. After a sequential hole filling process for the entire binary pattern (step 114) has completed, the modified binary pattern is stored in the memory 71.

Next, the hole-filled binary pattern is read out of the memory 71 into the thinning circuit 76 in the preprocessing unit 72. The thinning circuit 76 operates to remove protrusions 40 on the circumference of the binary pattern as shown in (b) of FIG. 6 thereby to facilitate the following process. The thinning process is a process performed for a partial area of, for example, a 3-by-3 pixel matrix of the hole-filled binary pattern, in which if eight points out of nine (all points of the pixel matrix excluding the central point in question) include at least one "0" value at a reasonable position, the point in question is made to have a "0" value irrespective of its original value. After the thinning process (step 116) by the thinning circuit 76 has completed, the modified binary pattern is stored in the memory 71. The hole filling circuit and thinning circuit are disclosed in Japanese Patent Application Laid-open No. 58-87650.

Figure 15:
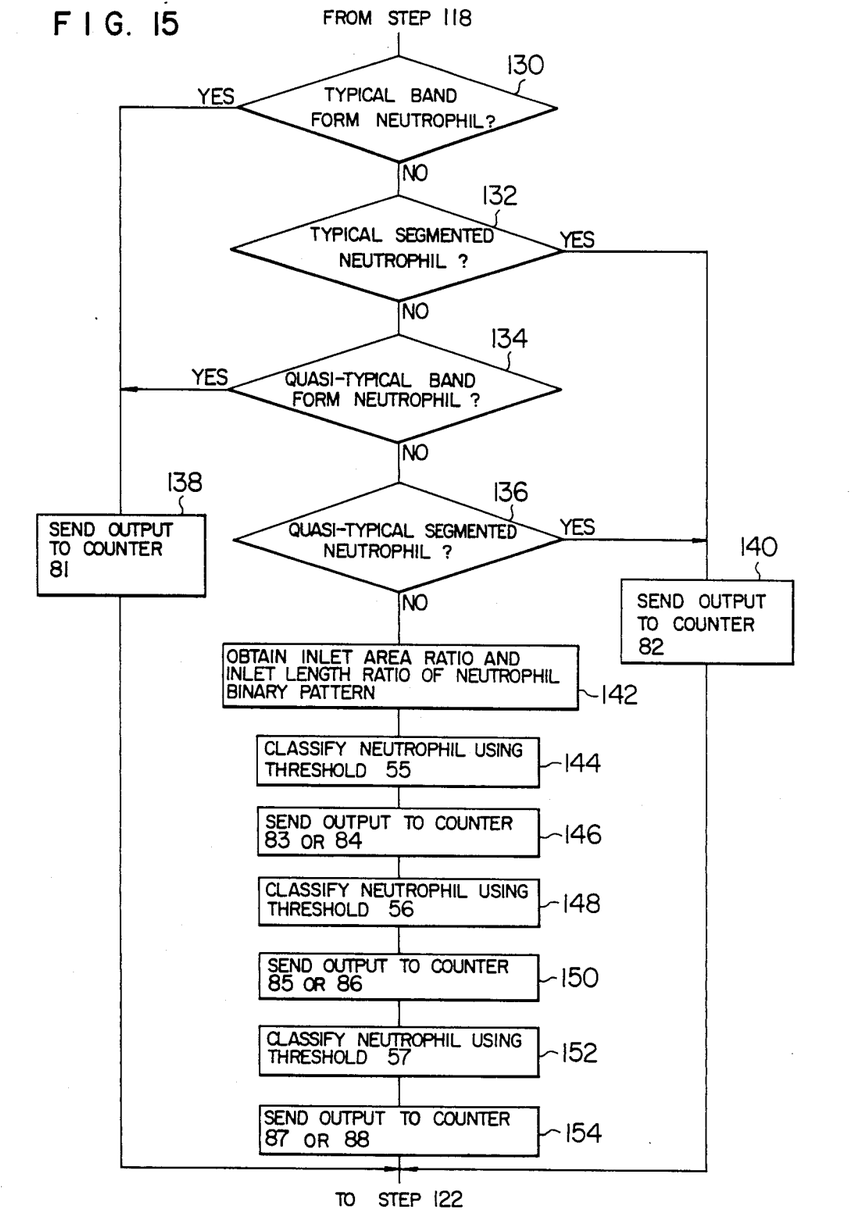

Subsequently, the binary pattern which has been rendered the thinning process is read out from the memory 71 into the control unit 77 via the preprocessing unit 72. The control unit 77 analyzes the shape of the preprocessed binary pattern in step 118, and determines through the pattern recognition process as to whether or not the sample leukocyte is a neutrophil. If it is determined to be a neutrophil, the control unit 77 further analyzes to determine as to whether the sample is a typical or quasi-typical band form neutrophil, a typical or quasi-typical segmented neutrophil, or a band form or segmented neutrophil in the intermixture domain (step 120, steps, 130-154 in FIG. 15). FIG. 15 shows in detail the process implemented in step 120 in FIG. 14.

As to whether or not the sample neutrophil is a typical or quasi-typical neutrophil is determined by the aforementioned method, and a sample which is not classified in any of these categories is determined to be a neutrophil in the intermixture domain.

Figure 13:
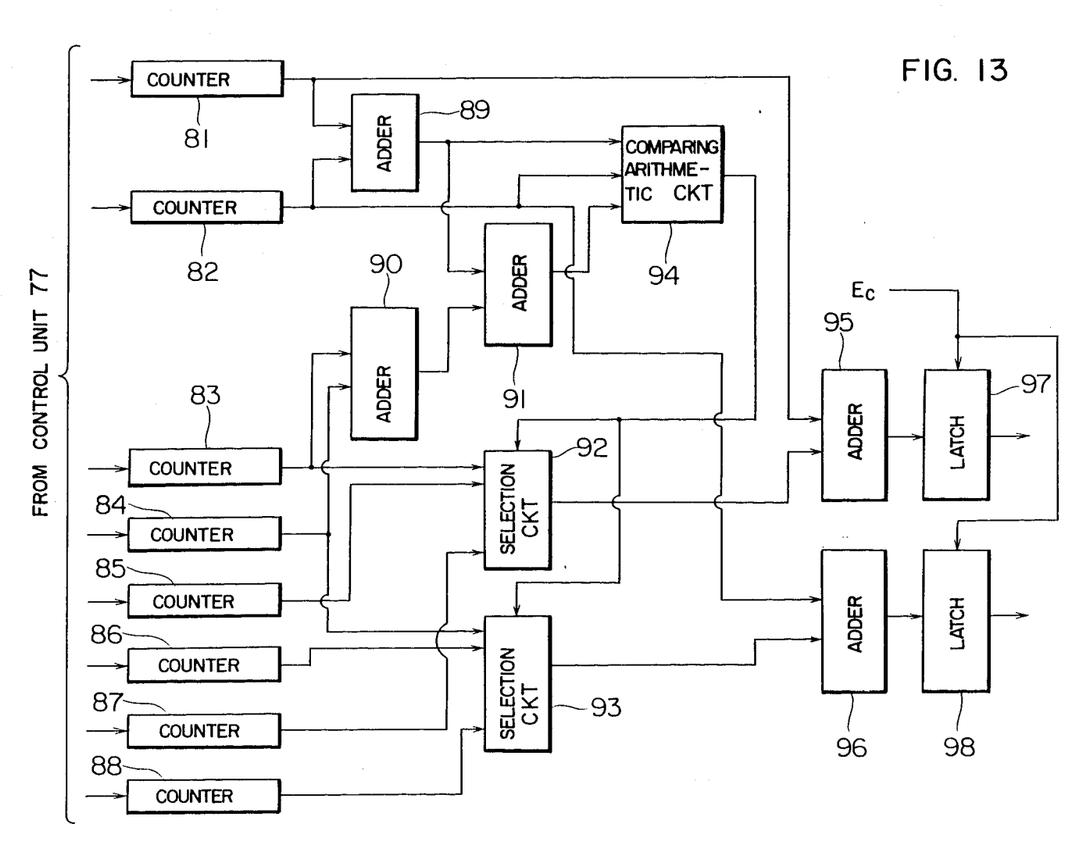
FIG. 13 is a detailed block diagram of the identification unit shown in FIG. 12.

If the sample leukocyte is determined to be a typical or quasi-typical band form neutrophil (steps 130 and 134), the control unit 77 provides an output to a counter 81 in FIG. 13 (step 138), or if it is determined to be a typical or quasi-typical segmented neutrophil (steps 132 and 136), the control unit 77 provides an output to another counter 82 (step 140). Accordingly, a sample neutrophil which is given a negative decision in step 136 is classified as a neutrophil in the intermixture domain.

Once the sample is determined to be a neutrophil in the intermixture domain, the area ratio and length ratio of the inlet are calculated (step 142). In case the threshold 55 is selected in accordance with the calculated area ratio and length ratio, determination is made as to whether the sample neutrophil is categorized to be a band form neutrophil or a segmented neutrophil, and the determination result is indicated to the corresponding counter 83 or 84 in FIG. 13 (steps 144 and 146). For example, if the sample is determined to be a band form neutrophil, it is indicated to the counter 83. The similar determination process takes place for the cases of the thresholds 56 and 57, and each determination result is indicated to the corresponding counter (steps 148-152).

Upon completion of analysis for one leukocyte, the counter in the control unit 77 is incremented by one (step 122), and unless the counter content n does not reach the predetermined value M as tested in step 124, the same analyzing procedure is carried out repeatedly until the analysis for all of M leukocytes completes. When the number of leukocytes processed (including neutrophils, eosinophils, monocytes, etc.) has reached the predetermined value M, the control unit 77 issues the end signal (Ec) to the classification unit 78 (step 126). On receiving the end signal Ec from the control unit 77, the classification unit 78 calculates the indeces Rn and Rm basing on the numbers of typical and quasi-typical, band form and segmented neutrophils, and selects one of the thresholds 55, 56 and 57 in FIG. 10 depending on the indeces Rn and Rm. Then, the classification unit 78 reads the count result in counters in FIG. 13 in correspondence to the selected threshold and determines the numbers of band form neutrophils and segmented neutrophils in the intermixture domain, and adds these numbers to the numbers of typical or quasi-typical band form neutrophils and typical or quasi-typical segmented neutrophils, respectively, so as to produce the final classification result. It should be noted that the numerical functions shown as graphs in FIGS. 10 and 11 are stored in a memory (e.g., RAM) within the control unit 77.

FIG. 13 shows in block diagram the arrangement of the classification unit 78 shown in FIG. 12. The arrangement includes counters 81-88, adders 89-91, selection circuits 92 and 93, a comparing arithmetic circuit 94, adders 95 and 96, and latches 97 and 98 for holding the final classification result. The number of outputs from the control unit 77 is counted by counters 81-88 corresponding to the classification.

First, typical or quasi-typical band form neutrophils are counted by the counter 81, which provides the value of denominator, $Bt+Bq$, for the expression (11). In the same way, typical or quasi-typical segmented neutrophils are counted by the counter 82, which provides the value of $St+Sq$ for the expressions (10) and (11). The counts provided by the counters 81 and 82 are entered to the adder 89 and at the same time delivered to the latches 95 and 96, respectively.

Next, neutrophils which have been determined to be those in the intermixture domain by the control unit 77 are counted by the counters 83-88 in correspondence to the thresholds 55, 56 and 57 shown in FIG. 10. Ones classified to be band form neutrophils based on the threshold 55 are counted by the counter 83, while ones classified to be segmented neutrophils are counted by the counter 84. The outputs of the counters 83 and 84 are entered to the adder 90, and at the same time fed to the selection circuits 92 and 93, respectively. Ones classified to be band form neutrophils based on the threshold 56 are counted by the counter 85, while ones classified to be segmented neutrophils are counted by the counter 86. The outputs of the counters 85 and 86 are fed to the selection circuits 92 and 93, respectively. Ones classified to be band form neutrophils based on the threshold 57 are counted by the counter 87, while ones classified to be segmented neutrophils are counted by the counters 87 and 88. The outputs of the counters 87 and 88 are fed to the selection circuits 92 and 93, respectively.

The adder 89 sums up the outputs of the counters 81 and 82 so as to provide the total number of typical and quasi-typical band form neutrophils and typical and quasi-typical segmented neutrophils, $Bt+Bq+St+Sq$. The adder 90 sums up the outputs of the counters 83 and 84 to provide the total number of neutrophils in the intermixture domain, $N-(Bt+Bq+St+Sq)$. The outputs of the adders 89 and 90 are entered to the adder 91, which sums up the values and provides the total number of neutrophils, N.

The outputs of the counter 82, adder 89 and adder 91 are entered to the comparing arithmetic circuit 94, which provides an output such as, for example, "0", "1" or "2" representing the region 61, 62 or 63 in the presumption space shown in FIG. 11. Namely, the circuit 94 calculates the value of Rn from the output $(St+Sq)$ of the counter 82 and the output N of the adder 91 using equation (10), and calculates the value of Rm from the output $(St+Sq)$ of the counter 82 and the output $(Bt+Bq+St+Sq)$ of the adder 89 using equation (11). By the comparison process for the values of Rn and Rm and the predetermined thresholds 64 and 65, it is determined to which region, 61, 62 or 63, of FIG. 11 the point determined from Rn and Rm belongs. The comparing arithmetic circuit 94 provides for the selection circuits 92 and 93 a "0" value when the point is determined to belong to the region 61 for a smaller number of band form neutrophils, a "1" value when the point is determined to belong to the region for a fairly large number of band form neutrophils, or a "2" value when the point is determined to belong to the region 63 for an extremely large number of band form neutrophils. The comparing arithmetic circuit 94 may be arranged as a table of threshold data stored in a memory so that one of the regions 61–63 is pointed by looking up the table in terms of the values of Rn and Rm.

The selection circuit 92 operates to select one of the outputs of the counters 83, 85 and 87 for counting band form neutrophils in the intermixture domain, while the selection circuit 93 operates to select one of the counters, 84, 86 and 88 for counting segmented neutrophils in the intermixture domain, both in response to the output of the comparing arithmetic circuit 94. The circuits 92 and 93 provide the selected outputs to the adders 95 and 96, respectively. Namely, the selection circuits 92 and 93 select the outputs of the counters 83 and 84, respectively, in response to a "0" output from the comparing arithmetic circuit 94, select the outputs of the counters 95 and 96 in response to a "1" output, or select the outputs of the counters 87 and 88 in response to "2" output from the circuit 94.

The adder 95 sums up the output of the counter 81 $(Bt+Bq)$ and the output of the selection circuit 92 (the count of band form neutrophils in the intermixture domain), and delivers the result to the latch 97. The adder 96 sums up the output of the counter 82 $(St+Sq)$ and the output of the selection circuit 93 (the count of segmented neutrophils in the intermixture domain), and delivers the result to the latch 98. The adders 89, 90, 91, 95 and 96 and the comparing arithmetic circuit 94 carry out the arithmetic processes while the classification of leukocytes is being processed by the control unit 77.

The latch 97 latches the output of the adder 95 and the latch 98 latches the output of the adder 96 in response to the end signal Ec from the control unit 77. In consequence, the total number of band form neutrophils out of M leukocytes is held in the latch 97, while the total number of segmented neutrophils out of M leukocytes is held in the latch 98.

The result of automatic classification using the foregoing inventive leukocytes classification apparatus was estimated to achieve a 83% coincidence with the result of manual classification, indicating a significant improvement when compared with a 74% coincidence achieved by the conventional method.

According to the present invention, as described above, neutrophils are classified accurately into band form neutrophils and segmented neutrophils irrespective of the proportion of neutrophils with linking or overlapping nuclei, whereby the accuracy of classification of neutrophils sampled in various conditions can be improved.

We claim:

1. An apparatus for classifying leukocytes comprising:

sample image preprocessing means for modifying the pattern of a nucleus of each of predetermined number of leukocytes extracted from an image of a blood sample;

analyzing means for analyzing each of the processed nucleus patterns and broadly classifying each of said leukocytes into a typical band form neutrophil, quasi-typical band form neutrophil, typical segmented neutrophil, quasi-typical segmented neutrophil, or other neutrophil in an intermixture domain or a leukocyte other than a neutrophil;

means for producing an index representing a relation among the number of said typical and quasi-typical band form neutrophils, the number of said typical and quasi-typical segmented neutrophils and the total number of neutrophils that have been broadly classified;

means for classifying each of the neutrophils in said intermixture domain into either a band form neutrophil or a segmented neutrophil in accordance with said index; and means for adding the numbers of band form and segmented neutrophils in said intermixture domain to the numbers of typical or quasi-typical band form and typical or quasi-typical segmented neutrophils, respectively thereby obtaining the total number of band form neutrophils and the total number of segmented neutrophils in the extracted leukocytes.

2. An apparatus for classifying leukocytes according to claim 1, wherein said index comprises two indexes representing different ratios among the number of said typical and quasi-typical band form neutrophils, the number of said typical and quasi-typical segmented neutrophils and the total number of neutrophils.

3. An apparatus for classifying leukocytes according to claim 2, wherein one of said two indexes is a ratio of the number of the typical and quasi-typical segmented neutrophils to the total number of the neutrophils, and another one of said estimation indexes is a ratio of the number of the typical and quasi-typical segmented neutrophils to the sum of the numbers of the typical and quasi-typical band form and segmented neutrophils.

4. An apparatus for classifying leukocytes according to claim 2, wherein said classifying means sets at least two threshold levels, each for classifying each of the neutrophils in the intermixture domain into a band form neutrophil or a segmented neutrophil, with respect to parameters of patterns of nucleus of neutrophils, selects one of said threshold levels in accordance with said two indexes, and classifies each of the neutrophils in said intermixture domain in view of the pattern of the nucleus thereof into a band form neutrophil or a segmented neutrophil in accordance with the selected threshold level.

5. An apparatus for classifying leukocytes according to claim 4, wherein said parameters are an inlet area ratio based on an area of a first inlet to the total area of inlet and an inlet length ratio based on the length of a common side to the length of all sides excluding the common side of a nucleus of a neutrophil pattern.

6. A method of classifying leukocytes comprising:
   a first step of quantizing an image of a blood sample obtained by opto-electro transducing the image to store the quantized image into a memory as quantized data;
   a second step of modifying the pattern of a nucleus of each of said predetermined number of leukocytes extracted from said quantized data;
   a third step of analyzing each of the processed nucleus patterns and broadly classifying each of said leukocytes into a typical band form neutrophil, quasi-typical band form neutrophil, typical segmented neutrophil, quasi-typical segmented neutrophil, or other neutrophil in an intermixture domain or leukocyte other than a neutrophil;
   a fourth step of calculating two indexes each representing a ratio among the number of said typical and quasi-typical band form neutrophils, the number of said typical and quasi-typical segmented neutrophils and the total number of neutrophils from the numbers of said typical and quasi-typical neutrophils and the total number of neutrophils based on said broad classification;
   a fifth step of classifying each of the neutrophils in said intermixture domain into a band form neutrophils or a segmented neutrophil in accordance with said two indexes; and
   a sixth step of adding the numbers of band form and segmented neutrophils in said intermixture domain to the numbers of typical or quasi-typical band form and typical or quasi-typical segmented neutrophils, respectively.

7. A method of classifying leukocytes according to claim 6, wherein one of said two indexes is a ratio of the number of the typical and quasi-typical segmented neutrophils to the total number of the neutrophils, and another one of said two indexes is a ratio of the number of the typical and quasi-typical segmented neutrophils to the sum of the numbers as the typical and quasi-typical band form and segmented neutrophils.

8. A method of classifying leukocytes according to claim 6, wherein said fourth step includes:
   setting at least two threshold levels, each for classifying each of the neutrophils in the intermixture domain into a band form neutrophil or a segmented neutrophil, with respect to parameters of patterns of nucleus of neutrophils;
   selecting one of said threshold levels in accordance with said two indexes; and
   classifying each of the neutrophils in said intermixture domain in view of the pattern of the nucleus thereof into a band form neutrophil or a segmented neutrophil in accordance with the selected threshold level.

9. A method of classifying leukocytes according to claim 6, wherein said parameters are an inlet area ratio based on an area of a first inlet to the total area of inlet and an inlet length ratio based on the length of a common side to the length of all sides excluding the common side of a nucleus of a neutrophil pattern.

* * * * *